(12) United States Patent
Graumann et al.

(10) Patent No.: US 7,491,940 B2
(45) Date of Patent: Feb. 17, 2009

(54) HIGH ENERGY RADIATION DETECTOR DEVICE

(75) Inventors: Rainer Graumann, Höchstadt (DE); Sven-Martin Sutter, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/694,042

(22) Filed: Mar. 30, 2007

(65) Prior Publication Data
US 2007/0228283 A1 Oct. 4, 2007

(30) Foreign Application Priority Data
Mar. 31, 2006 (DE) .................. 10 2006 015 027

(51) Int. Cl.
*G01T 1/166* (2006.01)
(52) U.S. Cl. ................. 250/363.05; 250/363.08; 250/368
(58) Field of Classification Search ........... 250/363.05, 250/363.08, 368
See application file for complete search history.

(56) References Cited

U.S. PATENT DOCUMENTS

| | | | |
|---|---|---|---|
| 4,987,585 A | | 1/1991 | Kidd et al. |
| 6,147,352 A * | 11/2000 | | Ashburn ................ 250/363.05 |
| 6,255,655 B1 | 7/2001 | | McCroskey et al. |
| 6,940,941 B2 * | 9/2005 | | Gregerson et al. ............ 378/4 |
| 2003/0058984 A1 | 3/2003 | | Susami et al. |
| 2004/0217292 A1 | 11/2004 | | Moyers et al. |
| 2004/0258210 A1 | 12/2004 | | Ritter |
| 2005/0218330 A1* | 10/2005 | | Rose et al. ................. 250/368 |
| 2007/0221852 A1* | 9/2007 | | Lusser ................... 250/363.05 |

OTHER PUBLICATIONS

Patent Abstracts of Japan Publication No. 2005249509 A.

* cited by examiner

*Primary Examiner*—Constantine Hannaher
(74) *Attorney, Agent, or Firm*—Schiff Hardin LLP

(57) ABSTRACT

In a device for capturing high energy radiation emitted from a radiation source within an examination object with a detector, the detector is arranged on a carriage mechanism that is mounted in a rotatable fashion around the examination object. The carriage mechanism is supported on a stand unit via a retaining mechanism, with an amplifier device being provided that amplifies the signals coming from the detector that are fed to the amplifier device via a signal guidance device. A data processing device is provided to process the amplified signals. By arranging the amplifier device and/or the data processing device essentially within the stand unit, a device is provided which can be flexibly utilized and which increases the patient's comfort during an examination.

10 Claims, 2 Drawing Sheets

HIGH ENERGY RADIATION DETECTOR DEVICE

BACKGROUND OF THE INVENTION

1. Field of the Invention

The invention relates to a device for capturing high energy radiation emitted from a radiation source within an examination object by means of a detector. Such a device is used in nuclear medicine.

2. Description of the Prior Art

In the field of nuclear medicine, which represents a technically highly developed subarea of medical engineering, radiation energies in the region of 70 kiloelectronvolts (keV), and higher are applied to perform examinations and treatments. Clinically widespread applications of nuclear medicine take the form of single photon emission computed tomography (SPECT) and positron emission tomography. The radiation used for SPECT and PET is gamma radiation, i.e. high energy electromagnetic radiation, and so is generally higher in energy than x-ray radiation. In order to generate the requisite gamma rays, SPECT uses radioactive decay processes of substances that are bound to tracers in which gamma rays are emitted and which are administered to the examination object via an oral, intravenous or respiratory route prior to the examination. With PET, the examination object is likewise administered a radioactive substance that decays while emitting positrons, i.e. by means of decay known as beta-plus decay. The positrons emitted by the radioactive substance then annihilate in the examination object with the resulting electrons producing characteristic gamma radiation.

The tracer or radioactive substance usually participates in the examination object's metabolism that is to be examined and thus becomes concentrated in certain tissue of the examination object, this tissue being deeply involved in the metabolism. A specific tracer is selected according to the purpose of the examination. For instance, various types of tumor can be identified using glucose tracers, because tumors reveal a higher energy consumption and therefore a higher glucose consumption than the surrounding tissue. The gamma rays generated directly or indirectly by means of the radioactive substances usually emerge, weakened by absorption, from the examination object. The gamma rays emerging from the patient permit a static and/or dynamic record of concentrations and where applicable depletions of gamma radiation sources in specific regions of the body, thus providing an indication of the metabolic function of the specific regions of the body, in particular organs, of the examination object.

The radioactive substances used for PET emit positrons and neutrinos, though only the positrons are of significance. If a positron strikes an electron in the environment—i.e. the examination object—the two annihilate producing two gamma quanta having an energy of 511 keV or 511 kiloelectronvolts and moving in exactly opposite directions. The exactly opposite direction of the two gamma quanta and the specific energy of the gamma quanta are based on the energy conservation law as well as on the law of conservation of momentum and angular momentum, which are also applicable for such events. The two gamma quanta are captured by means of a detector. For the purpose of the analysis, only such detection events are used in which gamma quantum detection has taken place on opposite detectors at essentially the same time. This is referred to as coincidence measurement.

A further difference between SPECT and PET is that the gamma rays required for the examination are produced differently—in SPECT they are produced directly by radioactive decay and in PET they are produced indirectly by positron-electron annihilation. In SPECT, the representation of the distribution of the radiation sources in the examination object, which can be reconstructed from the captured gamma rays, shows the distribution of the radioactive substance in the examination object, whereas in PET it yields the distribution of the annihilation sites of positrons and electrons.

To detect the gamma rays emerging from the body in PET and SPECT, at least one ray detector that can be rotated around the examination object is operated to capture the gamma rays in a specific solid angle area. Since, statistically, radiation is emitted randomly in all directions when the tracer radioactively decays, regardless of whether it is gamma radiation or positron radiation, SPECT devices as well as PET devices usually are constructed such that the radiation detectors each cover a solid angle area which is as large as possible around the area of examination of the patient. In this way it is possible to detect an as large as possible proportion of gamma radiation emerging from the examination area.

Conventional detectors used for this purpose primarily are scintillation detectors. Semiconductor detectors such as cadmium zinc telluride detectors are now increasingly used. When the gamma rays strike a scintillation crystal incorporated within a detector, for example sodium iodide (NaI) doped with thallium (Tl), electron processes will be triggered by the incident gamma rays. These processes excite the luminescent centers of the scintillation crystal and the gamma rays are converted into low energy electromagnetic radiation, usually in the visible spectral range. The optical signal is then usually converted into an electrical signal, e.g. by a photodetector. The electrical signal is then amplified. The conversion and amplification are usually carried out within a common apparatus, for example by a photomultiplier.

With appropriate capturing of gamma rays, both SPECT and PET make it possible to determine a spatial representation of the distribution of the gamma radiation sources in the examination object. A further application of SPECT and PET is to examine metabolic functions in living organisms, particularly in specific organs, with cranial vascular diseases, tumors and receptor diseases such as coronary heart diseases, etc.

United States Application Publication 2004/0217292 discloses a positron emission tomography apparatus which has continuously rotating detectors. The positron emission tomography apparatus has two or more detectors that are arranged on a rotating carriage system in a removable fashion. Each detector includes an array of scintillators which is connected to a light guide. The light guide is in turn connected to an array of photodetectors, with the result that the optical signals generated by the scintiliator array are converted into electrical signals. Each detector furthermore incorporates data processing electronics for the purpose of processing the electrical signals fed thereto. Such a positron emission tomography apparatus is disadvantageous because the device is very heavy, is expensive to purchase and occupies considerable space. Furthermore, such positron emission tomography apparatuses are usually set up at a stationary operating location and can cause anxiety in patients because they have to be in an enclosed space.

SUMMARY OF THE INVENTION

An object of the invention is to provide a device for capturing high energy radiation emitted from a radiation source within an examination object by means of a detector, which can be deployed in a flexible manner and that increases the patient's comfort during an examination.

This object is achieved by a device for capturing high energy radiation emitted from a radiation source within an examination object by means of a detector, the detector being arranged on a carriage mechanism that is mounted in a rotatable fashion around the examination object, the carriage mechanism being supported on a stand unit by a retaining mechanism, with an amplifier device being provided which amplifies the signals from the detector that are fed to the amplifier device via a signal guidance device, and having a data processing device that processes the amplified signals, the amplifier device and/or data processing device being arranged essentially within the stand unit.

The inventive arrangement allows a large part of the weight of the inventive device to be transferred into the stand unit, thus increasing the stability and rapidity of the device. As used herein a "stand unit" means the unit essentially bearing the weight of the device, this unit preferably being configured as a self-contained structure, optionally including a housing. Moreover, costs can be saved during the manufacture of the device, since respective amplifier units and/or data processing devices are not provided for each detector. The device according to the invention is furthermore advantageous because the weight of the detectors mounted in a rotatable fashion around the examination object is reduced, which means it is possible to rotate the detectors around the examination object more rapidity, thus reducing the examination time. With the inventive embodiment of the detectors it is also possible to increase examination comfort, because the device is designed so that it does not enclose the examination object.

Examination objects are usually understood to include all living organisms, preferably plant and animal multiple-cell entities. The radioactive substances administered to the examination object in a PET application can differ from those in a SPECT application. Gamma-radiating radioactive substances are exclusively used for the SPECT application, and pure positron-radiating substances are used for the PET application. It is possible, however, to use radioactive substances for PET and SPECT applications, with these substances emitting positrons as well as releasing gamma rays when they decay. Technetium 99 m methyl diphosphonate is an example of such a substance, which is often used for bone scintigraphs.

The gamma rays emerging from the body are detected by means of one or more detectors. Scintillation detectors are often used as such detectors due to their high quantum yield and sensitivity. With this type of detector it is possible to choose whether to forward the detected signal to the amplifier unit as an optical or electrical signal. The scintillation crystal or crystals convert an incident gamma quantum into a plurality of low energy light quanta, frequently within the visible spectral range. These light quanta can now be forwarded to the amplifier device by means of a signal guidance device set up for this purpose—for instance an optical wave guide. Alternatively, an optical signal supplied by the detector can be converted into an electrical signal prior to the signal being forwarded to the amplifier device, and then as an electrical signal it can be forwarded to the amplifier device by means of a signal guidance device configured for this purpose. If the first case is implemented, it is possible to further reduce the weight of the detectors, as only one optical conductor is provided to transmit the detector signals supplied by the detector. In the latter case, however, at least one conversion device is provided on each detector, the conversion device converting the optical signal into an electrical signal and thus increasing the weight of the detectors.

The inventive amplifier device or number of amplifier devices essentially arranged within the stand unit amplifies a signal fed thereto. The entire decoding electronics, i.e. one or more amplifier devices and one or more data processing devices, are preferably arranged essentially within the stand unit. The signal comes from the at least one detector and can be processed on its way from the detector to the amplification device via further devices and methods. An electrical signal can be amplified, for example, using conventional transistors. An optical signal can be amplified by an optical amplifier. Electrical signals can furthermore be converted into optical signals and vice versa by an electro-optical converter. It is advantageous to use an electro-optical converter in combination with an amplifier function, for example a large area avalanche photo diode (LAAPD), since such an arrangement is cost-effective and established. This diode has a high quantum yield in the visible spectral range and ensures internal signal amplification by exploiting a charge-related avalanche effect. A LAAPD is therefore very suitable for converting an optical signal into an amplified electrical signal.

The optical signal is not usually amplified as such, but instead the optical signal is initially converted into an electrical signal and the electrical signal is then amplified. However, an amplifier device for an optical signal is also possible, so that an amplified optical signal is then either used directly for the data processing or, in its amplified form, is converted into an electrical signal and made available for a conventional data processing device working with electrical signals.

If the gamma rays are captured using detectors for a large number of varying projection geometries, in particular recording directions, which can be adjusted by rotating the detectors around the examination object, it is possible to determine a spatial representation of the distribution of gamma radiation sources in the examination object using the data processing device. A spatial representation of the determined distribution of gamma radiation sources in the examination object can in particular be superimposed on a spatial representation of the anatomy of the relevant area of the body.

In an embodiment of the invention, the retaining mechanism includes a guide unit to retain and/or guide the carriage mechanism, with a signal coupling point being provided between the guide unit and carriage mechanism. By means of the guide unit, the carriage mechanism, to which at least one detector is attached, can be moved freely around the examination object within the scope of the provided guide, and in particular rotated. The provided signal coupling point can have more than one functionality. The purpose of the signal coupling point is inter alia to enable the signals to be forwarded between two adjacent device components that are movable in relation to each other. The signal coupling point can be configured for electrical or also for optical signals. The signals supplied by the various detectors, where more than one detector is used, preferably converge at the signal coupling point.

Depending on the number of adjacent device components that are directly or indirectly involved in forwarding signals and that are movable in relation to each other, it is possible to provide more than one signal coupling point. The electrical or optical signals are injected via the signal coupling point into a signal guidance device running preferably within the adjacent device component. In some instances after passing through further signal coupling points, the signal is finally guided to the amplifier device essentially arranged within the stand unit or to a conversion and amplifier device. The amplified signals then undergo data processing in the data processing unit also arranged essentially in the stand unit.

In an embodiment of the invention, the signal guidance device is configured as an optical wave guide. In this way, it is also possible to feed an optical signal supplied by, for instance, a scintillation detector as an optical signal of the amplifier device or conversion and amplifier device. The optical wave guide is preferably adjusted to the wavelength emitted by the scintillation crystal, so that the optical signal is forwarded with as little loss as possible. Glass, quartz or plastic fibers can be used as material for the optical wave guide. Transmitting an optical signal via an optical wave guide is advantageous compared with transmitting an electrical signal with an electrical conductor because optical wave guides can be laid virtually arbitrarily parallel to other supply cables. There is no electromagnetic interference to affect other signal lines. The optical transmission also enables the signal to be conducted without radiating noise. Distance-related losses of the signal due to inductance, capacitance and resistance do not occur with optical wave guides. Furthermore, optical wave guides sustain far higher data transfer rates than electrical conductors, e.g. by using different wavelengths for optical signals while simultaneously ensuring signal transmission.

When using optical signals, varying wavelengths can be assigned to the signals supplied by the various gamma ray detectors, it then being possible to inject and parallel process the wavelengths in the signal coupling point together into the optical wave guide leading to the amplifier device or to the conversion and amplifier device. This increases the rate at which the data is processed and thus evaluated. Due to the usually low signal attenuation of the optical signal while it is being guided through an optical wave guide, only a negligible reduction in signal amount is to be expected when transmitting the optical signal coming from the detector possibly via the signal coupling device to the conversion and/or amplifier device.

In an embodiment of the invention, at least one amplifier unit is provided to reduce a loss in the amount of the optical signal guided through the optical wave guide. Such an amplifier unit can be combined with a signal coupling point which is possibly provided. The amplifier unit is thus embodied as an optical amplifier. Optical amplifiers can directly or indirectly amplify an optical signal. "Direct amplification" as used herein means the amplification of an optical signal without converting it into an electrical signal. "Indirect amplification" is used herein to mean amplification via double electro-optical conversion of an optical signal and intermediate electrical amplification. Amplification of the signal via an amplifier unit can be required if an optical wave guide is not sufficiently adjusted to the wavelength used, giving rise to high signal attenuation. Having to span long signal transmission distances can be a further reason for such amplification.

In another embodiment of the invention, the amplification device is configured as a photomultiplier. The photomultiplier acts as a means of converting the optical signal into an electrical signal and then amplifying the electrical signal. A photomultiplier thus embodies a conversion and amplifier device for an optical signal fed to the photomultiplier. An arriving light quantum or photon releases one or more electrons out of the back of a cathode by photoelectric effect. The electron(s) are accelerated toward a first dynode by a high voltage, with further electrons being released from the first dynode as a result of the accelerated electrons striking the first dynode. A first amplification of the signal thus takes place. The electrons produced via the first dynode are now accelerated toward a second dynode via a further potential gradient, releasing further electrons from the second dynode. By arranging more than one dynode one after the other, it is possible to amplify the signal by several orders of magnitude. An optical signal is thus transferred into an amplified electrical signal by a photomultiplier. In view of its sensitivity and field of application, the photomultiplier is a proven measuring instrument for light quanta in the visible spectral range and is frequently used to record optical signals or to amplify signals, with technical service personnel usually having considerable experience with respect to this amplifier device As stated above, an alternative to the photomultiplier in the form of large area avalanche photodiode has since become available, though it has not yet been possible to implement this alternative in the field of PET and SPECT.

In a further embodiment of the invention, the data processing device is embodied such that a spatial representation of the radiation source arranged within the examination object can be determined from the signals. The data processing device thus makes it possible to determine and represent a spatial distribution of the locations of the gamma ray formation from the gamma rays that are emitted from the radiation sources within the examination object and captured with varying projection geometries. To this end it is possible to implement reconstruction methods, as known for example in x-ray technology, which can be stored in the data processing device. In this way it is possible to obtain data for example on the metabolism of the examination object.

In a preferred embodiment of the invention, the carriage mechanism is configured in a C-shape, U-shape or L-shape. This means that the stand unit, retaining mechanism and carriage mechanism can essentially be incorporated in x-ray devices constructed in the same way. Where necessary, SPECT, PET and x-ray devices can use the same stand unit, retaining mechanism and carriage mechanism. Only the x-ray tube and optionally a detector are therefore replaced to incorporate the respective application as a SPECT, PET or x-ray application. Replacing a detector is necessary if a detector arranged on the carriage mechanism is not suitable for detecting gamma rays or x-rays with the requisite precision and sensitivity. It is therefore possible to save costs by combining the use of the stand unit for SPECT, PET and x-ray devices. Configuring the PET or SPECT device as a C-arm, U-arm or L-arm system enables diverse possible applications in PET and SPECT. Furthermore, a number of options can be provided for capturing data to determine a spatial distribution of gamma radiation sources, for example by angular rotation, orbital rotation, combined angular and orbital rotation. This increases the flexibility of use of the device and presents new possible applications for such a device, such as use during surgical interventions on an examination object, as is standard in x-ray technology.

In a further embodiment of the invention, exactly two detectors are arranged on a carriage mechanism opposite each other and aligned in parallel with each other. This corresponds to an arrangement of device components as is known for example in C-arm x-ray devices, but with at least the x-ray tube being replaced with a detector that is suitable for detecting gamma rays. Two detectors are therefore mounted on a C-arm opposite each other, arranged in parallel and usually aligned with each other, so it is possible to move the C-arm around the examination object in a variety of ways. By arranging the detectors thus, which is also possible for example with carriage mechanisms configured as a U-arm and C-arm, two-dimensional projection representations of the radiation source distribution can be determined in the examination object, as well as spatial representations. To this end, the data captured by both detectors is preferably superimposed in a single projection representation, to increase the intensity and optionally reduce the interference of random emission behavior from the radiation sources. Such a device can be used for PET as well as for SPECT.

In a further embodiment of the invention, the stand unit is mounted on roller elements. The SPECT or PET device can be embodied as a movable arrangement by inventively disposing the amplifier device and/or data processing device essentially within the stand unit and additionally mounting the stand unit on roller elements. New fields of application are thus presented for SPECT and in particular for PET examinations, for example with medical interventions or with bedridden patients. A possible field of application is detecting residual tumors while performing surgery to remove a tumor

DESCRIPTION OF THE PREFERRED EMBODIMENTS

Figure 1:
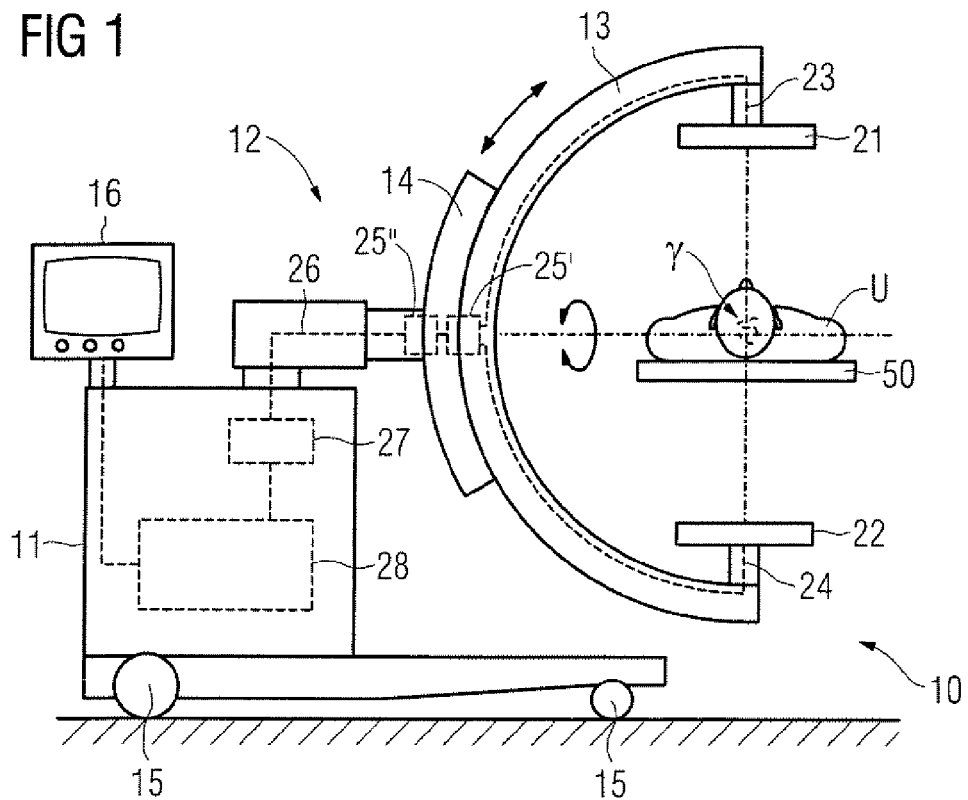
FIG. 1 is a side view of a movable device for performing positron emission tomography.

FIG. 1 shows a side view of a movable device 10 for performing positron emission tomography. The device 10 comprises a stand unit 11 and a carriage mechanism 13, with the carriage mechanism 13 being configured as a C-arm. The C-arm 13 is supported via a retaining mechanism 12 on the stand unit 11. The retaining mechanism 12 has a guide unit 14, on which the C-arm 13 is mounted. The C-arm 13 can be orbitally rotated in a motorized fashion using the guide unit 14, Furthermore, the retaining mechanism 12 is configured such that it enables at least one rotation of the C-arm 13 around a horizontal axis of angulation running in a C-arm plane extending from the C-arm 13. The retaining mechanism 12 can additionally comprise mechanisms that provide further degrees of freedom for the movement of the retaining mechanism 12, for example for a parallel displacement of the C-arm 13. The stand unit 11 is mounted on roller elements 15, which are embodied as cylindrical rollers. In this way, the PET device 10 is movable or mobile.

A first gamma ray detector 21 and a second gamma ray detector 22 are arranged on the C-arm 13. The detectors 21 and 22 are configured as scintillation detectors, so that the detector emits an optical signal when gamma rays strike the detector surface. The detectors 21 and 22 are positioned opposite each other on the C-arm 13 and are aligned in such a way that the detection surfaces of detectors 21 and 22 run parallel to each other. It is therefore possible to carry out a coincidence measurement required to perform positron emission tomography for the gamma rays striking the detector surface of detectors 21 and 22.

When positron emission tomography is performed, an examination object U supported on a patient-supporting device 50 is arranged between the first detector 21 and the second detector 22. A positron-emitting substance has previously been administered to the examination object U. The positron-emitting substance distributes itself within the examination object in a characteristic fashion. The examination object U thus has a spatial distribution of positron radiation sources. Gamma rays that are characteristic for such a process are produced by the annihilation of positrons exiting from the radioactive substance distributed in the examination object U with electrons usually coming from examination object U. These gamma rays can be assigned gamma radiation sources γ that correspond to the annihilation points of the respective positrons and electrons. The spatial distribution of positron radiation sources therefore usually differs from the spatial distribution of gamma radiation sources γ, as a positron initially covers a free wavelength in the examination object U, before it annihilates with an electron in two gamma quanta flowing in opposite directions.

The gamma quanta emerging from the examination object U in opposite directions are detected by the detectors 21 and 22 arranged opposite each other on the C-arm 13, provided they exit the examination object U in a suitable solid angle area. The gamma quanta therefore strike the respective detector surface of the detectors 21 or 22 and enter the scintillation crystal used in the exemplary embodiment for the detection of gamma rays. The gamma quanta are converted into low energy radiation, usually in the visible spectral range, by means of the scintillation crystal, e.g. a cesium iodide or sodium iodide crystal doped with thallium. This process takes place for a large number of gamma quanta emerging from the examination object U, the quanta being captured by detectors 21 and 22.

As shown in FIG. 1, the optical signals provided by detector 21 or 22 are guided from the first detector 21 or the second detector 22 to an optical signal coupling point 25' by means of a first optical wave guide 23 and a second optical wave guide 24. The signal coupling point 25' and the optical wave guide 23 or 24 are configured such that the optical signals of the detectors 21 and 22 can reach the signal coupling point 25' in any orbital position of the C-arm 13. It is thus possible to arrange signaling panels or signaling interfaces, which are not shown, for example on the outside of the C-arm 13 or on the back of the C-arm 13, such panels or interfaces being connected to a signal coupling point 25' arranged in the guide unit 14 in any rotation position of the C-arm 13. The optical signals of the detectors 21 and 22 are therefore brought out of the C-arm 13 and, as shown in FIG. 1 and are fed into a further signal coupling device 25" arranged between the guide unit 14 and an adjacent component of the retaining mechanism 12. This signal coupling device 25" is used to transfer signals from the guide unit 14 of the C-arm 13 mounted in a rotatable fashion around an axis of angulation into a part of the retaining mechanism 12 that is rigid in position with respect to the stand unit 11. The optical signals of the second signal coupling point 25" are then guided by an optical wave guide 26 into the stand unit 11 toward the conversion and amplifier device 27, which is configured as a number of photomultipliers.

In some instances, to improve signal guidance, it is possible to provide multiplexers and demultiplexers (not shown in FIG. 1) to achieve serial or parallel signal processing of the optical signal. With such devices and associated methods, it is furthermore possible to keep the number of photomultipliers 27 small, thus reducing the cost of the device 10.

The respective optical signals from detector 21 or 22 are converted into an electrical signal by means of the photomultiplier 27 and are amplified for example by six orders of magnitude in accordance with the methods described above. The converted and amplified signals are then fed into a data processing device 28, which further processes the signals.

To determine the distribution of the gamma radiation sources γ in the examination object U, the C-arm 13 and thus the detectors 21 and 22 arranged on the C-arm 13 are orbitally rotated around the examination object U in a motorized fashion by means of the guide unit 14. The gamma rays emerging from the examination object U are captured in this way for a large number of different angle positions of the detectors 21 and 22 with respect to the examination object U. The signals supplied by the detectors 21 and 22 in the various angle positions are then fed into the data processing device 28, which uses them to reconstruct a spatial representation of the distribution of gamma radiation sources γ in the examination object U. The determined spatial representation of the distribution of gamma radiation sources γ can be output as a graphical representation on the input/output facility that includes a display 16.

Figure 2:
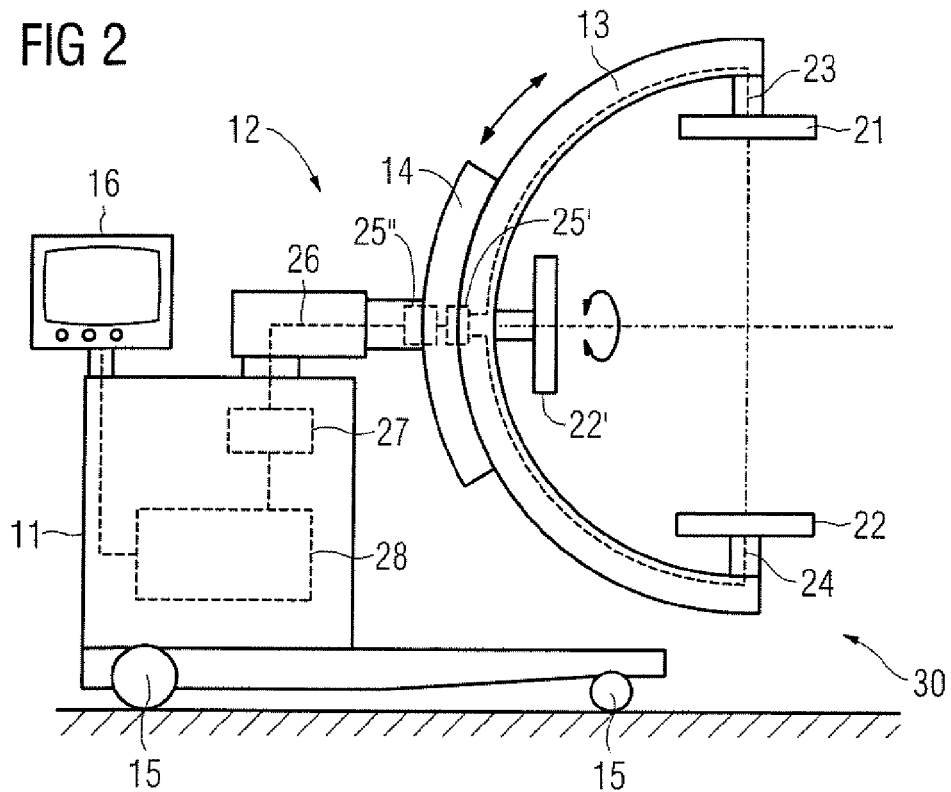
FIG. 2 is a side view of a device that can be used as a positron emission tomography apparatus or a single photon emission computed tomography apparatus.

FIG. 2 shows a device 30 that, in the same way as the device 10 shown in FIG. 1, can be used for performing single photon emission computed tomography as well as for performing positron emission tomography. The device 30 shown in FIG. 2 differs from the device 10 shown in FIG. 1 in that an additional detector 22' is arranged in the center between the first detector 21 and second detector 22 on the C-arm 13. Since there is no coincidence measurement taken in single photon emission computed tomography, it is possible for the detectors 21 or 22 or 22' used for single photon emission computed tomography not to be arranged opposite each other. By rotating the C-arm 13 for example orbitally around the examination object U (cf. FIG. 1) and thus the three detectors 21 or 22 or 22' arranged in accordance with FIG. 2, gamma rays emerging from the examination object U (cf. FIG. 1) can be captured at an angle of 360 degrees around the examination object U (cf. FIG. 1).

Figure 3:
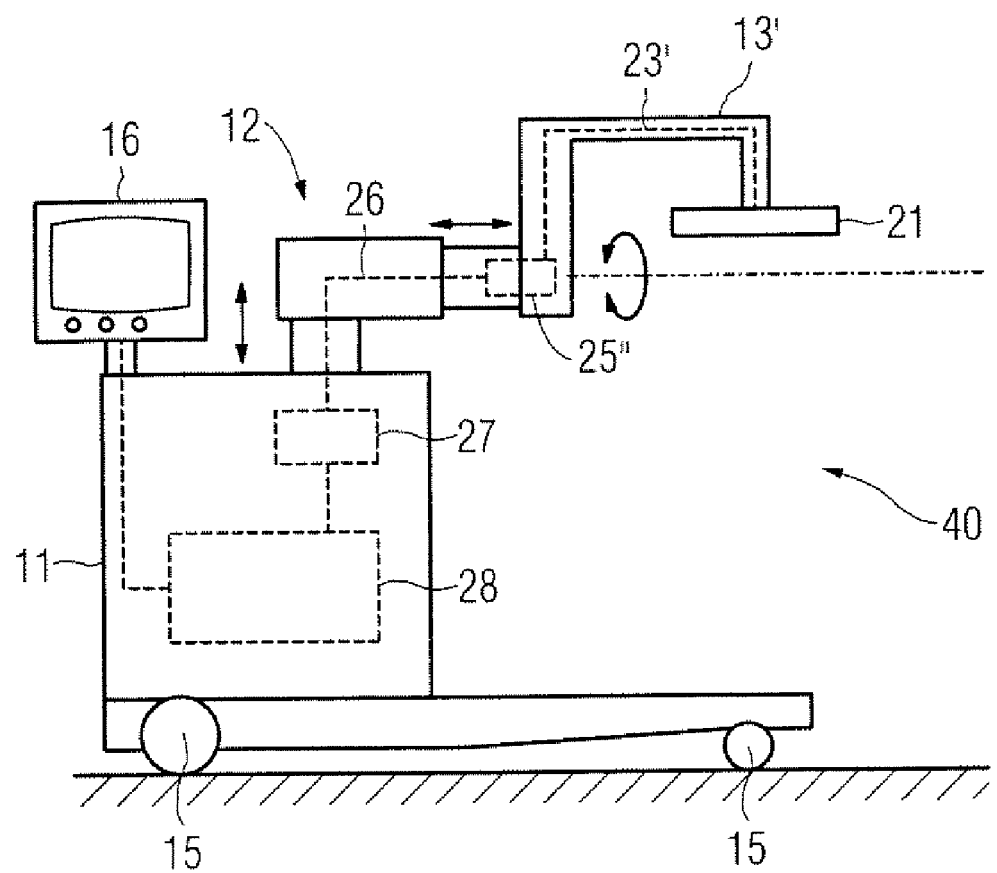
FIG. 3 is a side view of a single photon emission computed tomography apparatus.

FIG. 3 shows a device 40 that can be used for single photon emission computed tomography, but not for positron emission tomography, as it is not possible to take a coincidence measurement of detector events if there is only one detector 21 arranged on a carriage mechanism 13'. The device 40 comprises a stand unit 11 and a U-shaped carriage mechanism 13'. The U-shaped carriage mechanism 13' is supported by means of a retaining mechanism 12 on the stand unit 11. The U-shaped carriage mechanism 13' can be rotated at least around a horizontal axis of angulation running in a U-arm plane extending from the U-shaped carriage mechanism 13'. The U-shaped configuration of the carriage mechanism 13' means that it is not possible to perform an orbital rotary movement around an examination object, which is not shown. To determine a spatial distribution of gamma radiation sources distributed in an examination object, it is therefore only possible to use the axis of angulation in this configuration. To compensate for the reduced flexibility of use of the device 40 due to it not being possible for the U-shaped carriage mechanism 13' to rotate orbitally, the retaining mechanism 12 can be configured in a particularly versatile fashion, so that a height adjustment of the carriage mechanism 13' and various translation and rotation movement options of the carriage mechanism 13' are provided with respect to the stand unit 11.

The stand unit 11 of the device 40 shown in FIG. 3 is mounted on cylindrical rollers 15, like the devices 10 and 30 shown in FIG. 1 and FIG. 2 respectively, so that the device 40 is movable, thereby achieving greater flexibility of use than in the case of previous SPECT and/or PET devices, as the device 40 can be utilized in various locations.

A gamma ray detector 21 is arranged on the U-shaped carriage mechanism 13', the detector having a detector surface aligned such that gamma rays exiting from the examination object can be captured in a solid angle area that is as large as possible. In some instances, the detector surface of the detector 21 can also be curved, thus further increasing the solid angle area covered by the detector 21.

The gamma rays captured by the detector 21 are fed as an optical signal via an optical wave guide 23 to a first signal coupling point 25" from where they are fed to a conversion and amplifier device 27 via a further optical wave guide 26. With the device 40 shown in FIG. 3, it is possible to avoid having a further signal coupling point, as it is not necessary to extract the optical signal from an orbitally rotating carriage mechanism 13, as shown in FIG. 1 or FIG. 2.

The optical signal is converted into an electrical signal and amplified in the conversion and amplifier device 27, which is configured as a photomultiplier. The amplified electrical signal is then fed into a data processing device 28, which further processes the signals.

By angularly rotating the detector around an examination object not shown in FIG. 3, gamma rays can be captured for a large number of varying camera axes with respect to the examination object. Using this data, it is then possible to determine a spatial distribution of the gamma radiation sources within the examination object, which in SPECT corresponds to the distribution of the radioactive substance emitting the gamma rays.

To capture gamma rays, it is also possible in principle to use detectors that do not operate in accordance with the scintillator principle, for example CdZnTe semiconductor detectors. With such detectors, an electrical signal is generated directly by the gamma rays striking the detector. With detectors of this kind it is therefore possible to produce a similar design to one of the devices 10, 30 or 40 shown in FIG. 1, 2 or 3 respectively for electrical instead of for optical signals.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for capturing high energy radiation emitted from a radiation source within an examination object, comprising:

first, second and third high energy radiation detectors, each configured to detect high energy radiation emitted by a radiation source within an examination object, each detector emitting output signals corresponding to high energy radiation detected by the detector;

a carriage mechanism comprising a support arm having two separated, non-contacting free ends, with said first and second detectors mounted respectively at said free ends, and said third detector being mounted on said arm approximately midway between said free ends, said support arm being configured to encompass, between said free ends, no more than 180° around the examination subject;

a stand unit having a retaining mechanism engaging said carriage mechanism to rotate at least said support arm and said detectors mounted on said support arm around the examination object in a rotation at range that causes said first, second and third detectors, in combination, to detect said high energy radiation emitted by said radiation source within the examination object throughout 360° around the examination object;

an amplifier device that amplifies said output signals from each detector to produce amplified signals;

a signal guidance device that conveys said output signals from each detector to said amplifier device;

a data processing device connected to said amplifier device that processes said amplified signals;

at least one of said amplifier device and said data processing device being contained substantially within said stand unit; and said stand unit engaged with said carriage mechanism forming a mobile unit.

2. A device as claimed in claim 1 wherein said retaining mechanism comprises a guide unit connected to said carriage mechanism, and a signal coupling point between said guide unit and said carriage mechanism via which said output signals are coupled between said guide unit and said carriage mechanism.

3. A device as claimed in claim 1 wherein detector is configured to emit optical signals as said output signals, and wherein said signal guidance device is an optical waveguide.

4. A device as claimed in claim 3 wherein said amplifier device compensates for an attenuation of said optical signals occurring due to said optical signals being guided through said optical waveguide.

5. A device as claimed in claim 4 wherein said amplifier device is a photomultiplier.

6. A device as claimed in claim 1 wherein said data processing device is configured to determine a spatial representation of said radiation source within said examination object from said amplified signals supplied thereto.

7. A device as claimed in claim 1 wherein said support arm of said carriage mechanism is C-shaped.

8. A device as claimed in claim 1 wherein said stand unit comprises roller elements allowing mobility of said stand unit on a floor.

9. A device as claimed in claim 1 wherein said data processing device is configured to process amplified signals, supplied from said amplifier device, from only said first and second detectors to generate a PET image of the examination object.

10. A device as claimed in claim 1 wherein said data processing device is configured to process amplified signals, supplied from said amplifier device, from each of said first, second and third detectors to generate a SPECT image of the examination object.

* * * * *